United States Patent
Ingwer et al.

(10) Patent No.: US 11,759,197 B2
(45) Date of Patent: Sep. 19, 2023

(54) SYSTEMS AND METHODS FOR ANCHOR PLACEMENT

(71) Applicant: ARTHREX, INC., Naples, FL (US)

(72) Inventors: Zachary Ingwer, Naples, FL (US); Drew Osika, Naples, FL (US); George Paletta, Chesterfield, MO (US); Matthew Johnson, Bonita Springs, FL (US)

(73) Assignee: Arthrex, Inc., Naples, FL (US)

(*) Notice: Subject to any disclaimer, the term of this patent is extended or adjusted under 35 U.S.C. 154(b) by 278 days.

(21) Appl. No.: 17/062,839

(22) Filed: Oct. 5, 2020

(65) Prior Publication Data
US 2021/0015477 A1 Jan. 21, 2021

Related U.S. Application Data (62) Division of application No. 15/985,159, filed on May 21, 2018, now Pat. No. 10,828,021.

(51) Int. Cl.
| | | |
|---|---|---|
| *A61B 17/04* | (2006.01) | |
| *A61B 17/17* | (2006.01) | |
| *A61B 17/68* | (2006.01) | |
| *A61F 2/38* | (2006.01) | |

(52) U.S. Cl.
CPC .......... *A61B 17/0401* (2013.01); *A61B 17/17* (2013.01); *A61B 17/68* (2013.01); *A61F 2/38* (2013.01)

(58) Field of Classification Search
CPC ..... A61B 17/04; A61B 17/0401; A61B 17/17; A61B 17/68; A61F 2/38
See application file for complete search history.

(56) References Cited

U.S. PATENT DOCUMENTS

| | | | |
|---|---|---|---|
| 5,147,367 A | * | 9/1992 | Ellis ................... A61B 17/1728 606/329 |
| 6,342,057 B1 | | 1/2002 | Brace et al. |
| 7,029,477 B2 | | 4/2006 | Grimm |
| 7,591,850 B2 | | 9/2009 | Cavazzoni |
| 7,686,838 B2 | | 3/2010 | Wolf et al. |
| 7,931,655 B2 | | 4/2011 | Axelson et al. |
| 8,439,926 B2 | | 5/2013 | Bojarski et al. |
| 9,084,618 B2 | | 7/2015 | Serbousek et al. |
| 9,138,219 B2 | | 9/2015 | Horrell et al. |
| 9,433,425 B2 | | 9/2016 | Wilkinson |
| 9,636,100 B2 | | 5/2017 | Wyman et al. |
| 9,855,062 B2 | | 1/2018 | Blum |

(Continued)

FOREIGN PATENT DOCUMENTS

| | | |
|---|---|---|
| EP | 1302167 A2 | 4/2003 |
| JP | 2008149180 A | 7/2008 |

(Continued)

OTHER PUBLICATIONS

International Search Report and Written Opinion for Corresponding PCT Application No. PCT/US2019/030007, dated Jul. 12, 2019.

(Continued)

*Primary Examiner* — Christopher J Beccia
(74) *Attorney, Agent, or Firm* — Lathrop GPM LLP; Lisa Hillman (57) ABSTRACT

Methods and systems disclosed herein provide systems and methods for anchor placement.

10 Claims, 6 Drawing Sheets

(56) References Cited

U.S. PATENT DOCUMENTS

| | | |
|---|---|---|
| 9,955,980 B2 | 5/2018 | Norton et al. |
| 9,974,550 B2 | 5/2018 | Seitlinger et al. |
| 10,028,751 B2 | 7/2018 | Blank et al. |
| 10,828,021 B2 * | 11/2020 | Ingwer ............... A61B 17/1764 |
| 2009/0171355 A1 * | 7/2009 | Amis ........................ A61F 2/38 |
| | | 606/53 |
| 2010/0324566 A1 | 12/2010 | Rathbun et al. |
| 2017/0135733 A1 | 5/2017 | Donner et al. |
| 2018/0021035 A1 | 1/2018 | Bourque et al. |
| 2018/0280018 A1 | 10/2018 | Laprade |
| 2019/0192278 A1 * | 6/2019 | Smigielski ............ A61F 2/0805 |

FOREIGN PATENT DOCUMENTS

| | | |
|---|---|---|
| WO | 200182805 A1 | 11/2001 |
| WO | 2007035326 A2 | 3/2007 |
| WO | 2007107697 A1 | 9/2007 |

OTHER PUBLICATIONS

PCT International Application No. PCT/US2019/030007, International Preliminary Report on Patentability, dated Dec. 3, 2020, 8 pages.

* cited by examiner

SYSTEMS AND METHODS FOR ANCHOR PLACEMENT

PRIORITY

This application is a divisional of U.S. application Ser. No. 15/985,159, filed May 21, 2018, the entirety of which is incorporated herein by reference.

BACKGROUND

The disclosure herein generally relates to medical instruments and, more particularly, to medical instruments for anchor placement.

SUMMARY

Existing methods of repairing a joint can involve inserting one or more anchors into the joint. For instance, a knee joint may suffer from a capsular disruption in which the knee capsule is separated from a knee joint structure (e.g., a tibia or femur). Repairing the capsular disruption can include inserting one or more anchors through the knee joint capsule and into the knee joint structure, so as to secure the knee joint capsule to the knee joint structure. However, current methods of repairing a joint by inserting one or more anchors into the joint have various drawbacks. For instance, it can be difficult to both efficiently and accurately insert the one or more anchors at the desired location.

Methods and systems in accordance with the present disclosure provide systems and methods for anchor placement in a joint. In example embodiments, the disclosed systems can be used during repair of a capsular disruption in which a knee joint capsule is secured to a knee joint structure with one or more anchors.

In an example, a medical instrument is described. A medical instrument includes a drill guide having a proximal end and a distal end. A medical instrument can also include at least one reference guide attached to the drill guide, wherein the at least one reference guide is configured to be positioned at (i) a predetermined angle relative to the drill guide and (ii) a predetermined height from the distal end of the drill guide. The predetermined angle and the predetermined height may be predetermined to avoid particular anatomical structure(s) and/or to place an anchor in proximity of anatomical structure(s). For example, a predetermined angle and a predetermined height can cause the drill guide to avoid the tibial plateau and to have proximity to a knee joint line when the reference guide aligns with a piercing rod positioned below a meniscus and above a tibial plateau.

In another example, a medical instrument is described. A medical instrument includes a drill guide to define or select an anchor placement location and an anchor placement angle. A medical instrument can also include a reference guide attached to the drill guide to define or select a reference line beneath a meniscus and above a tibial plateau, wherein the anchor placement location has a predetermined offset from the reference line, and wherein the anchor placement angle has a predetermined angle relative to the reference line.

In another example, a method is described. A method includes inserting a piercing rod through a knee capsule, beneath a meniscus, and above a tibial plateau. A method can also include advancing a reference guide attached to a drill guide over the piercing rod, wherein the drill guide defines or identifies an anchor placement location that has a predetermined offset from the piercing rod. A method can also include advancing a drill pin through the drill guide and drilling a hole into a joint structure at the defined anchor placement location. A method can further include advancing an anchor through the drill guide and placing the anchor in the hole.

DETAILED DESCRIPTION

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein.

The disclosed medical instruments can be used in conjunction with surgical procedures that involve inserting one or more anchors into a joint. In an example, the disclosed instrument can be used in conjunction with surgical procedures in which the anchor(s) is to be inserted at an offset from a reference location in the joint that can be visualized during the procedure (e.g., visualized with an arthroscope). The disclosed instrument allows for inserting the anchor at a precise location and angle from the visualized reference location in the joint. An example surgical procedure in which the disclosed instrument can be used is described in U.S. patent application Ser. No. 15/596,015 (hereinafter "the '015 application"), the entire disclosure of which is incorporated herein by reference.

Figure 1A:
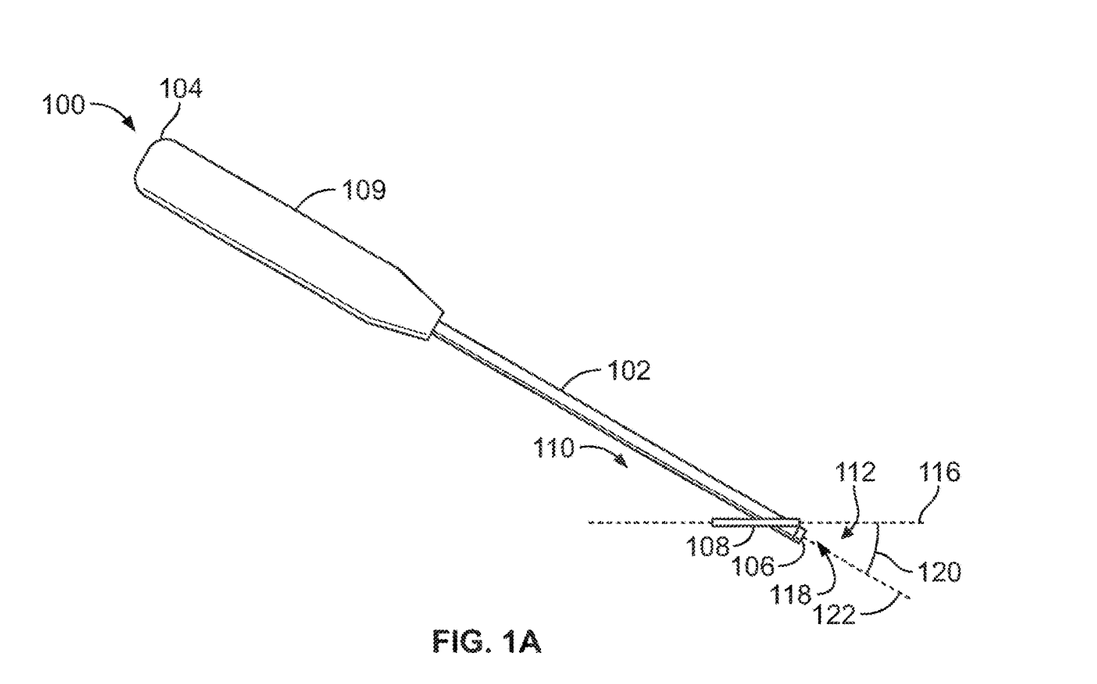
FIG. 1a illustrates a side view of an example medical instrument for anchor placement, according to an example embodiment.
Figure 1B:
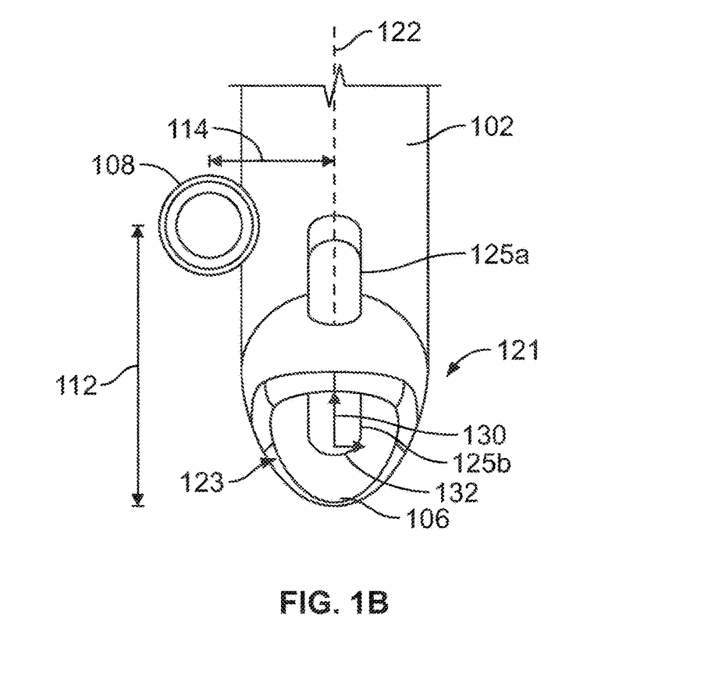
FIG. 1b illustrates a front view of the distal end of the medical instrument of FIG. 1a, according to an example embodiment.

Referring now to FIGS. 1a-b, an example medical instrument 100 for anchor placement is illustrated. The medical instrument 100 includes a drill guide 102 having proximal end 104 and a distal end 106. The medical instrument 100 also includes at least one reference guide 108 attached to the drill guide 102. The at least one reference guide 108 is positioned at a predetermined angle 110 relative to the drill guide 102 and a predetermined height 112 from the distal end 106 of the drill guide 102. The at least one reference guide 108 is also positioned at a predetermined lateral distance 114 (see FIG. 1b) from longitudinal axis 122 of the drill guide 102.

Any suitable materials can be used for these components of the medical instrument 100, including but not limited to metal, plastic, and/or rubber. In an example embodiment, the drill guide 102 and the at least one reference guide 108 comprise a medical-compliant metal, such as surgical-grade stainless steel. Other materials are possible as well. In the example shown, the medical instrument 100 also includes a handle 109 near the proximal end 104 of the drill guide 102. The handle 109 can provide an ergonomic grip to allow a surgeon to hold and maneuver the medical instrument 100 as needed during a surgical procedure.

In general, the drill guide 102 has a size and shape that allows the drill guide 102 to receive and surround a drill pin and/or an anchor. In an example embodiment, the drill guide 102 comprises a hollow tube. In an example embodiment, the hollow tube of the drill guide 102 is circular or substantially circular. In other examples, the hollow tube of the drill guide 102 comprises a polygon shape, such as a triangle, square, pentagon, hexagon, heptagon, octagon, nonagon, or decagon. Other shapes are possible as well.

The hollow tube of the drill guide 102 can include any suitable length, outer diameter, and inner diameter. In an example embodiment, the length is about 145 mm to about 215 mm (e.g., about 145, 155, 160, 165, 175, 180, 185, 190, 195, 200, 205, 210, or 215 mm (or any range from about 145 to about 215 mm)). In an example embodiment, the outer diameter is about 2.6 mm to about 5.6 mm (e.g., about 2.6, 2.8, 3.0, 3.5, 4.0, 4.5, 5.0, 5.5 or 5.6 mm (or any range from about 2.6 mm to about 5.6 mm)). In an example embodiment, the inner diameter is about 1.6 mm to about 4.1 mm (e.g., about 1.6, 2.0, 2.5, 3.0, 3.5, 4.0, and 4.1 mm (or any range from about 1.6 to 4.1 mm)). The outer and inner diameter of the hollow tube of the drill guide 102 are selected so that drill guide 102 is suitable for passage of drill pins and/or anchors without being too large so that it is unable to be used in the body.

In general, the at least one reference guide 108 has a size and shape that allows the at least one reference guide 108 to receive and surround a piercing rod. In an example embodiment, the reference guide 108 comprises a hollow tube. In an example embodiment, the hollow tube of the reference guide 108 is circular or substantially circular. In other examples, the hollow tube of the reference guide 108 comprises a polygon shape, such as a triangle, square, pentagon, hexagon, heptagon, octagon, nonagon, or decagon. Other shapes are possible as well.

The hollow tube of the reference guide 108 can include any suitable length, outer diameter, and inner diameter. In an example embodiment, the length is about 145 mm to about 215 mm (e.g., about 145, 155, 160, 165, 175, 180, 185, 190, 195, 200, 205, 210, or 215 mm (or any range from about 145 to about 215 mm)). In an example embodiment, the outer diameter is about 2.6 mm to about 5.6 mm (e.g., about 2.6, 2.8, 3.0, 3.5, 4.0, 4.5, 5.0, 5.5 or 5.6 mm (or any range about 2.6 mm to about 5.6 mm)). In an example embodiment, the inner diameter is about 1.6 mm to about 4.1 mm (e.g., about 1.6, 2.0, 2.5, 3.0, 3.5, 4.0, and 4.1 mm (or any range from about 1.6 to 4.1 mm)). The outer and inner diameter of the hollow tube of the reference guide 108 are selected so that the reference guide 108 is suitable for passage of a piercing rod without being too large so that it is unable to be used in the body.

In an example embodiment, the piercing rod is a needle. In another example embodiment, the piercing rod is a wire. In yet another example embodiment, the piercing rod is a pin. Other piercing rods are possible as well. A piercing rod can have a diameter of about 1 mm to about 2 mm and a length of about 125 to about 225 mm.

With reference to FIG. 1B, the tip 121 of the drill guide can include a rounded edge 123 and slits 125a-b. The slits can allow the user to visualize that the implant is fully seated in the bone by observing a laser line through the window.

The medical instrument 100 can be used in conjunction with surgical procedures that involve inserting one or more anchors into a joint, and is particularly suitable for surgical procedures in which the anchor(s) is to be inserted at an offset from a reference location in the joint that can be visualized (e.g., visualized with an arthroscope or other suitable device). With reference to FIG. 1a, the at least one reference guide 108 defines or identifies a reference line 116, and the drill guide 102 defines or identifies both an anchor placement location 118 and an anchor placement angle 120. The anchor placement location 118 has a predetermined offset from the reference line 116. The predetermined offset includes a predetermined vertical distance below the reference line 116 a predetermined lateral distance from the reference line 116. Furthermore, the anchor placement angle 120 has a predetermined angle relative to the reference line 116.

In a particular example, the medical instrument 100 can be used during a surgical procedure for repairing a capsular disruption in a knee joint, during which one or more anchors can be inserted through the knee joint capsule and into a knee joint structure (e.g., the tibia), so as to secure the knee joint capsule to the knee joint structure. In this surgical procedure, an arthroscope can be positioned to allow visualization of the knee joint capsule and the knee joint structure. Furthermore, a piercing rod can be placed through the skin and into the knee joint space, such that the piercing rod is below a meniscus and above a tibial plateau. The position of the piercing rod in the knee joint space can be visualized with the arthroscope to confirm that the piercing rod is below a meniscus and above a tibial plateau. The at least one reference guide 108 can then be advanced over the piercing rod until the drill guide 102 abuts the tibia. The predetermined angle and height of the at least one reference guide 108 cause the drill guide 102 to avoid a tibial plateau and to have proximity to a knee joint line when the reference guide 108 aligns with a piercing rod positioned below a meniscus and above a tibial plateau. The reference guide 108 aligns with the piercing rod when the reference guide 108 slides over the piercing rod.

In an example embodiment, the proximity to the knee joint line provided by the angle and height of the reference guide 108 is a vertical distance below the knee joint line of about 1 mm to about 5 mm. Other distances are possible as well (e.g., about 0.1, 0.5, 1.0, 1.5, 2.0, 2.5, 3.0, 3.5, 4.0, 4.5, 5.0, 5.5, 6.0, 6.5, 7.0 mm, or more (or any range between about 0.1 and 7.0 mm)).

Medical instrument 100 can be configured to provide any desired predetermined offset (i.e., vertical distance and lateral distance) of the anchor placement location 118 from the reference line 116. As mentioned above, the at least one reference guide 108 has both a predetermined height 112 from the distal end 106 of the drill guide 102 and a predetermined lateral distance 114 from the longitudinal axis 122. In the example of FIG. 1b, the height 112 from the distal end 106 of the drill guide 102 is the distance from the distal end 106 along z-axis 130, and the lateral distance 114 from longitudinal axis 122 is the distance along the y-axis 132.

In an example embodiment, the predetermined height 112 is about 1 mm to about 5 mm. Since the height from the distal end 106 of the drill guide 102 about 1 mm to about 5 mm, the anchor placement location 118 will be between about 1 mm and about 5 mm below the reference line 116. Other predetermined heights 112 are possible as well (e.g., about 0.1, 0.5, 1.0, 1.5, 2.0, 2.5, 3.0, 3.5, 4.0, 4.5, 5.0, 5.5, 6.0, 6.5, 7.0 mm, or more (or any range from about 0.1 to 7.0 mm)).

In an example embodiment, the predetermined lateral distance 114 is about 0.5 mm to about 3 mm. This allows for defining an anchor placement location 118 that is laterally located (e.g., to the left or right along the y-axis 132) from about 1 mm to about 3 mm from the longitudinal axis 122. However, other predetermined lateral distances 114 are possible as well (e.g., about 0.1, 0.5, 1.0, 1.5, 2.0, 2.5, 3.0, 3.5, 4.0, 4.5, 5.0 mm, or more (or any range from about 0.1 to 5.0 mm)).

Medical instrument 100 can also be configured to include any desired predetermined anchor placement angle 120 from the reference line 116. In an example, the predetermined angle 110 relative to the drill guide 102 is about 15 degrees to about 60 degrees. In the example of FIGS. 1a-b, since drill guide 102 is substantially straight, predetermined angle 110 and anchor placement angle 120 will be the same or substantially the same. In an example, the reference line 116 is parallel or substantially parallel to the knee joint line, and thus the inserted anchor will be angled about 15 degrees to about 60 degrees relative to the knee joint line. Other predetermined angles relative to the drill guide 102 are possible as well (e.g., about 5, 10, 15, 20, 25, 30, 35, 40, 45, 50, 55, 60, 65, 70, 75, or more (or any range about 5 degrees to 75 degrees)).

Within examples, the at least one reference guide 108 is fixed to the drill guide 102. For instance, the at least one reference guide 108 illustrated in FIGS. 1a-b is fixed to the drill guide 102. The at least one reference guide 108 can be fixed to the drill guide 102 in any suitable fashion. In an example, the at least one reference guide 108 is welded to the drill guide 102. In another example, the at least one reference guide 108 is fixed to the drill guide 102 with a fastener and/or an adhesive. Other examples are possible as well.

Within examples, the at least one reference guide 108 is non-movably fixed to the drill guide, such that the at least one reference guide 108 is not adjustable or moveable relative to the drill guide 102. Within other examples, the at least one reference guide 108 comprises an adjustable reference guide that is moveable relative to the drill guide 102. The at least one reference guide 108 can be configured to have an adjustable angle, an adjustable height from the distal end 106 of the drill guide 102, and/or an adjustable lateral distance 114 from the longitudinal axis 122 of the drill guide 102.

Figure 2:
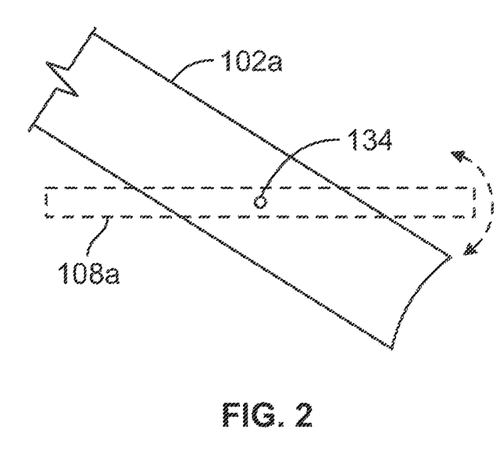
FIG. 2 illustrates a side view of a distal end of a medical instrument for anchor placement, according to an example embodiment.
Figure 3:
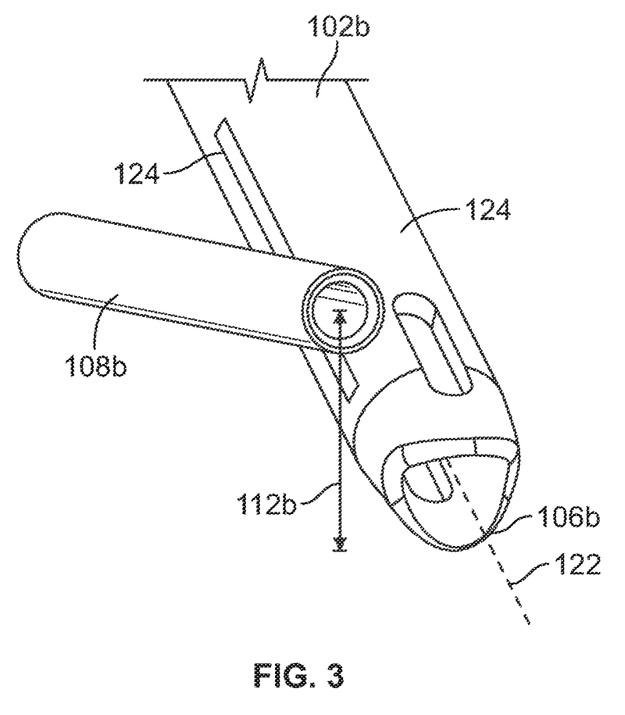
FIG. 3 illustrates a perspective view of a distal end of a medical instrument for anchor placement, according to an example embodiment.

In an example embodiment, the at least one reference guide 108 is an adjustable reference guide that is at least one of (i) moveable between a plurality of predetermined angles relative to the drill guide 102 or (ii) moveable between a plurality of predetermined heights from the distal end 106 of the drill guide 102. For instance, FIGS. 2 and 3 illustrate example adjustable reference guides. FIG. 2 illustrates a distal end of drill guide 102a having an adjustable reference guide 108a. The adjustable reference guide 108a is hingedly attached to the drill guide via hinge 134, such that the adjustable reference guide 108a can adjust its angle relative to drill guide 102a. In an example, the adjustable reference guide 108a includes a lock to secure the adjustable reference guide 108a at a desired angle. In an example, the lock comprises a fastener (e.g., a screw, pin, etc.) that locks the reference guide 108a at a desired angle.

FIG. 3 illustrates a distal end of drill guide 102b having an adjustable reference guide 108b. The adjustable reference guide 108b is slidable relative to a longitudinal axis 122 of the drill guide 102b to adjust the height 112b from the distal end 106b of the drill guide 102b. In an example, the drill guide 102b includes a slit 124 in the body 124, and the reference guide 108b is moveable along the slit 124. The reference guide 108b can be locked in position at any desired height. In an example embodiment, the adjustable reference guide 108b includes a lock to secure the adjustable reference guide 108b at any position along the slit 124. In an example, the lock comprises a fastener (e.g., a screw, pin, etc.) that locks the reference guide 108b at a desired height. In an example, the adjustable reference guide 108b is also moveable between a plurality of predetermined angles relative to the drill guide 102.

In a surgical procedure involving insertion of a plurality of anchors, the adjustability of the at least one reference guide 108 can allow the surgeon to use a single instrument for the insertion of all of the anchors.

Figure 4:
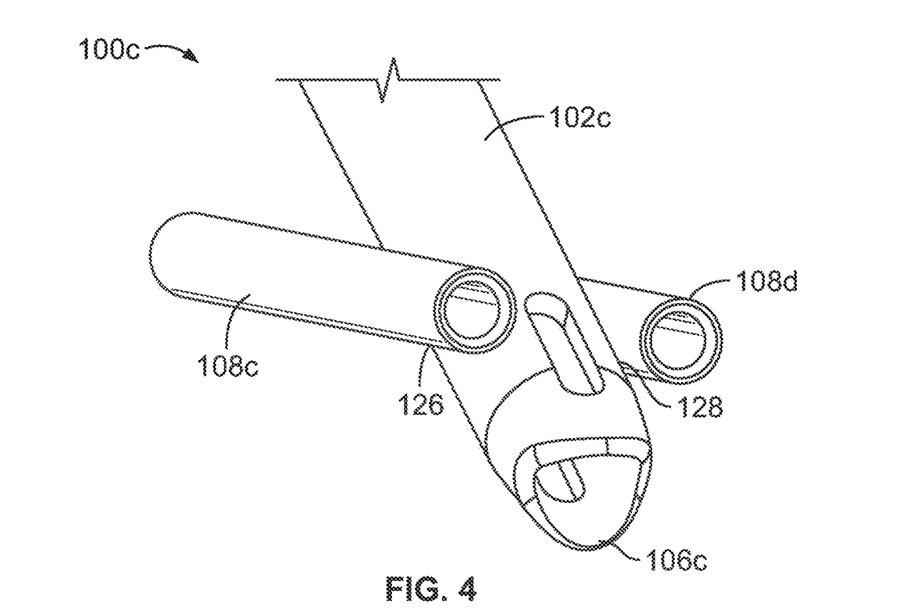
FIG. 4 illustrates a perspective view of a distal end of a medical instrument for anchor placement, according to an example embodiment.

In the examples of FIGS. 1a-3, the at least one reference guide 108 is a single reference guide. However, in other examples, the medical instrument 100 can include two or more reference guides attached to the drill guide 102. For instance, FIG. 4 illustrates a distal end of an example instrument 100c that includes drill guide 102c and reference guides 108c-d. Reference guide 108c is positioned at a first point 126 on the drill guide 102c, whereas reference guide 108d is positioned at a second point 128 on the drill guide 102c. In general, the first point 126 and the second point 128 can be at any suitable location on the drill guide 102c. In this example, the first point 126 is located about 180 degrees from the second point 128. Furthermore, in this example, the references guides 108c-d have different predetermined heights from the distal end 106c of the drill guide 102c. However, in other examples, the reference guides 108c-d can have the same predetermined height from the distal end 106c of the drill guide 102c. Within examples, the first point 126 is located about 100 degrees to about 180 degrees from the second point 128. In a surgical procedure involving insertion of two anchors, the two reference guides 108c-d can allow the surgeon to use a single instrument for the insertion of the two anchors.

Figure 5:
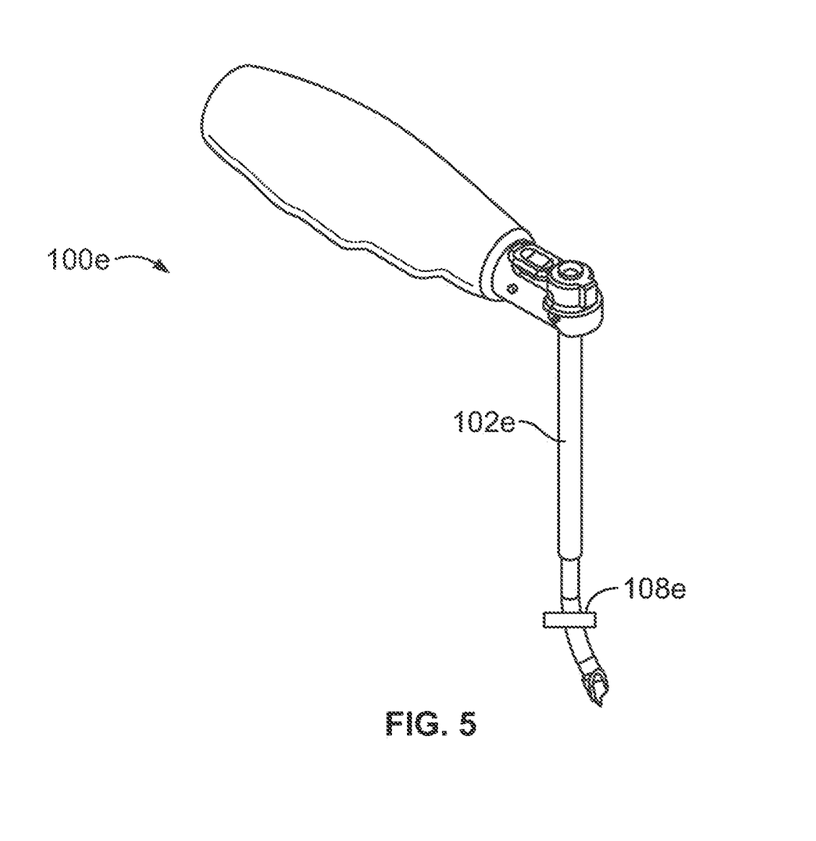
FIG. 5 illustrates a perspective view of an example medical instrument for anchor placement, according to an example embodiment.

In the examples of FIGS. 1a-4, the drill guide 102 is a straight or substantially straight drill guide. However, in other examples, the drill guide 102 could be a curved drill guide. An example medical instrument 100e having a curved drill guide 102e with attached reference guide 108e is shown in FIG. 5.

In accordance with example embodiments, methods for anchor placement are provided. As indicated above, within example embodiments, the medical instrument in accordance with the present disclosure can be used in the surgical procedures described in the '015 application. The example methods thus can be similar in some respects to the method of repairing a capsular disruption described in the '015 application with reference to FIGS. 5-14 at paragraphs [0037]-[0048]. However, the '015 application describes use of a conventional drill guide used to guide a drill pin and to place two anchors in the knee joint structure. For instance, the '015 application describes inserting a spinal needle into the joint space, determining a certain distance distal to this spinal needle for capsular repair on the tibia, and placing a conventional drill guide at this determined distance to guide a drill pin for drilling a hole for the anchor. In practice, a surgeon would have to visually estimate the desired location at which to place the conventional drill guide and/or introduce another instrument to assist with placing the conventional drill guide at the desired location. In accordance with embodiments of the present disclosure, rather than using the drill guide of the '015 application to guide the drill pin and to place the two anchors, one or more medical instruments 100 can instead be used to guide the drill pin and to place the two anchors at the desired location in the knee joint structure. Since the medical instrument 100 includes the reference guide attached to the drill guide, the medical instrument 100 allows for a more efficient and accurate anchor placement location than existing methods using a conventional drill guide.

An example of a method in which the drill guide of the '015 application is replaced with one or more medical instruments 100 can involve inserting a piercing rod through a knee capsule, beneath a meniscus, and above a tibial plateau. The example method can also involve advancing a reference guide attached to a drill guide over the piercing rod, wherein the drill guide defines or identifies an anchor placement location that has a predetermined offset (i.e., a vertical distance and a lateral distance) from the piercing rod. The example method can also involve advancing a drill pin through the drill guide and drilling a hole into a joint structure at the defined anchor placement location. The example method can also involve advancing an anchor through the drill guide and placing the anchor in the hole. This example method is described in detail below with reference to FIGS. 6-11. It should be understood that the many of the possibilities and permutations of the methods described in the '015 application can also apply to this example method described below.

Figure 6:
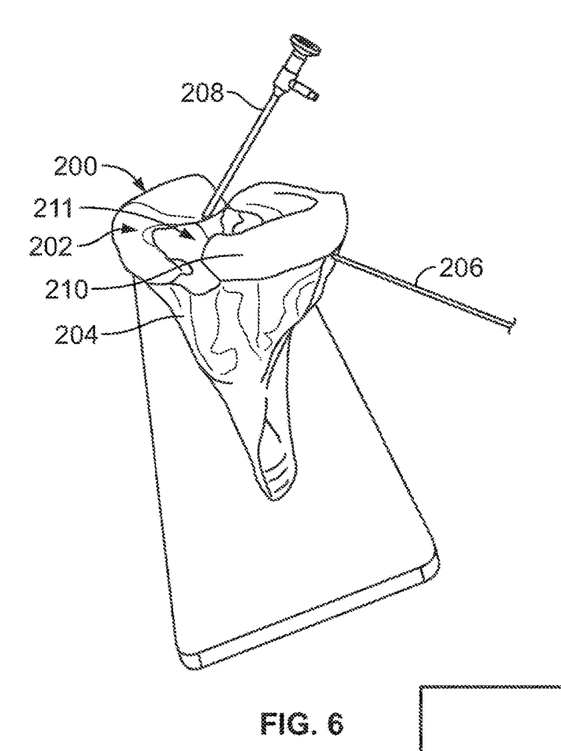
FIGS. 6-11 illustrate various example steps of method, according to an example embodiment.

FIG. 6 illustrates a knee 200 upon which the example method is performed. In this example, knee 200 is illustrated as a synthetic knee model. However, in other examples, the knee 200 is a knee of a patient. In yet other examples, the knee 200 is a cadaveric knee. The knee 200 includes a knee joint space 202 and a knee joint structure 204. The example method also involves inserting a piercing rod 206 into the knee joint space 202 and, in particular, through a knee capsule (not show), beneath meniscus 210, and above tibial plateau 211. An arthroscope 208 is also inserted into the knee joint space 202. The arthroscope 208 can allow for visualization of the knee joint space 202, the meniscus 210, and the knee joint structure 204. The example method also involves visualizing the piercing rod 206 with arthroscope 208 to confirm that the piercing rod 206 is located beneath meniscus 210 and above tibial plateau 211.

Figure 7:
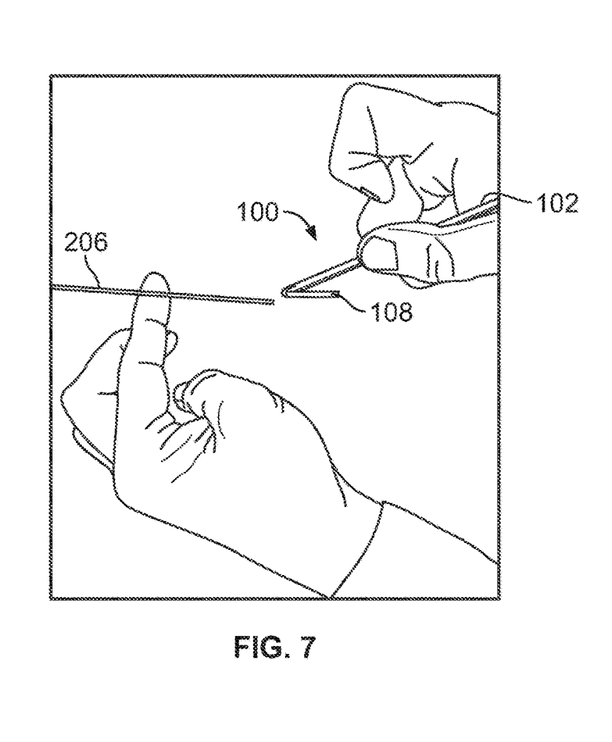
Figure 8:
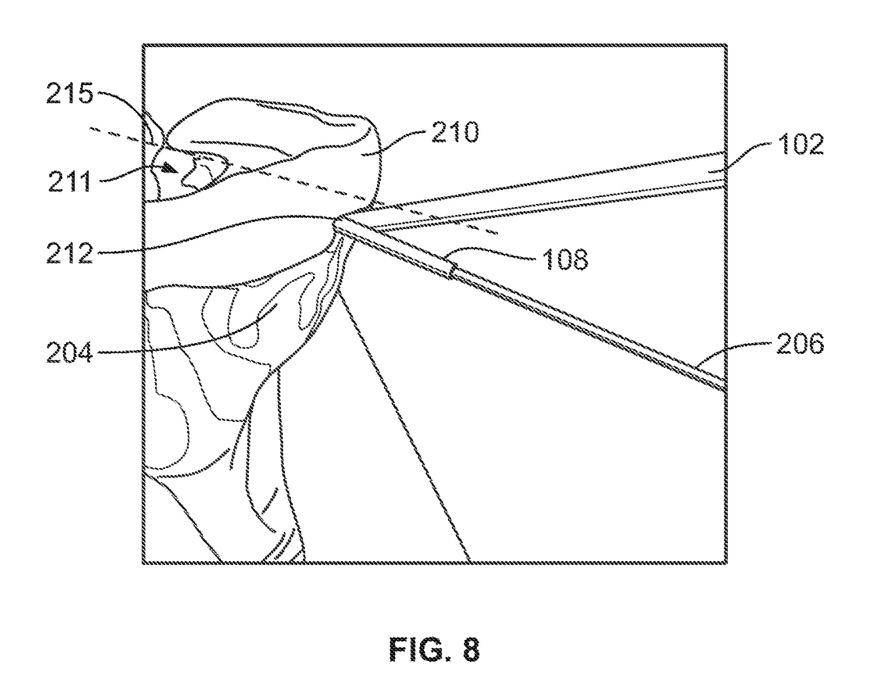

With reference to FIGS. 7-11, one or more of the medical instruments in accordance with the present disclosure can then be used for placement of one or more anchors at a predetermined offset from the piercing rod 206. As seen in FIGS. 7-8, medical instrument 100 is used for defining an anchor placement location and angle. In particular, the method involves placing the piercing rod 206 within the reference guide 108 and advancing reference guide 108 attached to drill guide 102 over the piercing rod 206. The reference guide 108 thus surrounds the piercing rod 206, and the reference guide 108 can be advanced over the piercing rod 206 until the drill guide 102 abuts the knee joint structure 204 (see FIG. 8). The drill guide 102 acts to define or select an anchor placement location 212 (see FIG. 8) that has a predetermined offset from the piercing rod 206. The predetermined offset allows for the drill guide 102 avoiding the tibial plateau 211 but having proximity to a knee joint line 215 (see FIG. 8) when the reference guide 108 aligns the piecing rod 206 below the meniscus 210 and above the tibial plateau 211.

Figure 9:
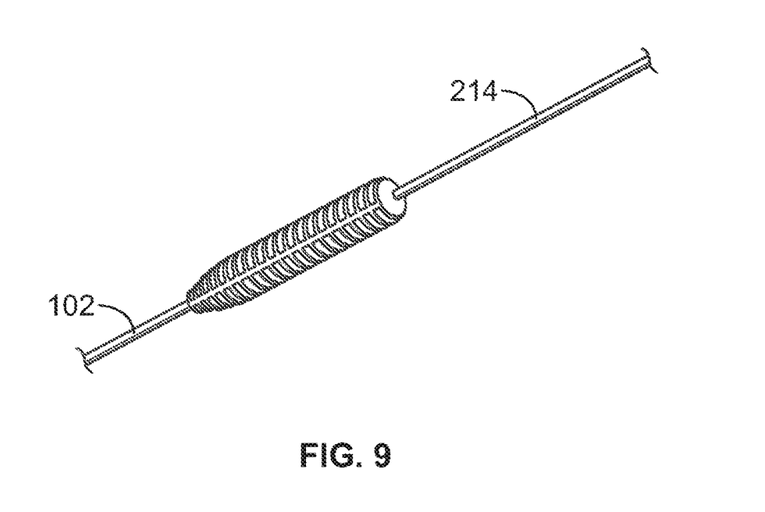
Figure 10:
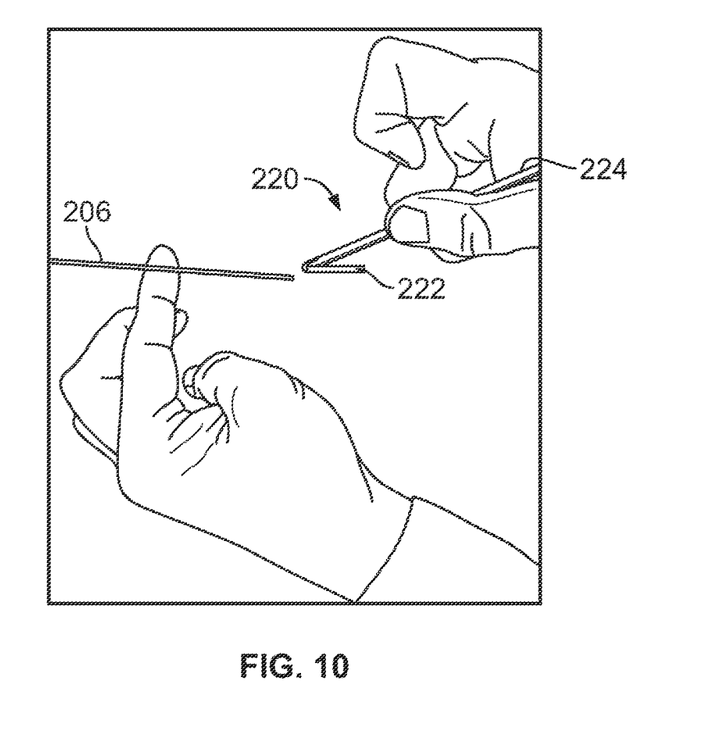
Figure 11:
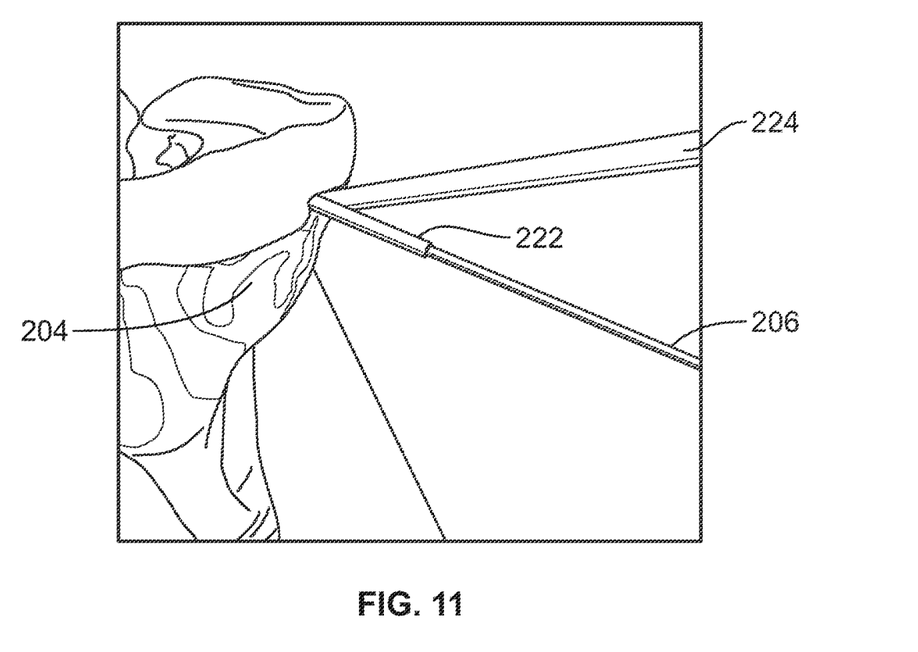

With reference to FIGS. 8-9, the method then involves advancing a drill pin 214 through the drill guide 102 (see FIG. 9) and drilling a hole into joint structure 204 at the defined anchor placement location 212 (see FIG. 8). With reference to FIG. 8, the method then involves advancing an anchor through the drill guide 102 and placing the anchor in the hole. Any suitable anchors are possible. For instance, in an example embodiment, the anchor is a suture anchor (knotless or knotted; e.g., a SutureTak® anchor, Quattro® Link knotless anchors, Twinfix® anchors, Bioraptor® anchors, Spyromite® anchors, Dynomite® anchors, Osteoraptor® anchors, Raptomite® anchors, JuggerKnot® anchors, JuggerKnotless® anchors, etc.), a soft tissue anchor (e.g., Eclipse™ soft tissue anchor, Piton™ soft tissue fixation implant, etc.), or the like. In another example, the anchor is a staple. Other anchors are possible as well.

The method can also involve inserting an additional anchor(s) into the joint structure 204. In an example embodiment, a second anchor is placed within about 2 cm of the first anchor. In a more particular example, the second anchor is about 1 to about 2 or about 1 to about 1.5 cm from the first anchor. However, other distances between the anchors are possible as well (e.g., about 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 cm, or more (or any range from about 0.3 to 3.0 cm)).

In an example embodiment, the additional anchor(s) can be inserted into the joint structure 204 using the same medical instrument 100. For instance, in an example, medical instrument 100 also includes a second reference guide attached to the drill guide 102 (e.g., reference guide 108*d* shown in FIG. 4). In this embodiment, the example method involves advancing the second reference guide 108*d* attached to the drill guide 102 over the piercing rod 206. In an example, the piercing rod 206 remains in the same location as the piercing rod 206 was positioned during the drilling of the first hole. In another example, the piercing rod 206 is removed and subsequently reinserted into knee joint space 202. The method then involves advancing drill pin 214 through the drill guide 102 and drilling a second hole into the knee joint structure 204 at the defined second anchor placement location, and advancing a second anchor through the drill guide 102 and placing the second anchor into the second hole.

In another example embodiment, the medical instrument 100 includes an adjustable reference guide (e.g., reference guide 108*b* shown in FIG. 3). In this embodiment, the method involves adjusting the reference guide 108*b* to a desired height to define or select a second anchor placement location. In an example, the reference guide 108*b* is removed from its alignment with the piercing rod 206 prior to the adjustment, and then re-aligned with the piercing rod 206 after the adjustment. In another example, the reference guide 108*b* can be adjusted while the reference guide 108*b* is aligned with the piercing rod 206. The method then involves advancing drill pin 214 through the drill guide 102 and drilling a second hole into the knee joint structure 204 at the defined second anchor placement location, and advancing a second anchor through the drill guide 102 and placing the second anchor into the second hole.

In another example embodiment, the additional anchor(s) can be inserted into the joint structure 204 using a different medical instrument for anchor placement. For instance, with reference to FIGS. 10 and 11, a second instrument 220 is provided. The second instrument 220 includes a second reference guide 222 attached to a second drill guide 224. The second drill guide 224 defines a second anchor placement location that has a second predetermined offset from the piercing rod 206. The method then involves advancing the second reference guide 222 attached to the second drill guide 224 over the piercing rod 206. The method then involves advancing drill pin 214 through the second drill guide 224 and drilling a second hole into the knee joint structure 204 at the defined second anchor placement location, and advancing a second anchor through the second drill guide 224 and placing the second anchor into the second hole.

As mentioned above, in an example embodiment, the one or more anchors secure the joint capsule to the joint structure 204 at a point of capsular disruption. The instrument(s) 100 to be used in the surgical procedure can be selected based on the particular capsular disruption being repaired. For instance, in an example embodiment, the method involves determining a distance of the point of capsular disruption from a position beneath the meniscus 210 and above the tibial plateau 211, and adjusting a position of the reference guide 108 relative to the drill guide 102 based the determined distance. Adjusting the position of the reference guide 108 relative to the drill guide 102 based the determined distance can involve adjusting the reference guide 108a or 108b (see FIGS. 2 and 3) to the desired position relative to the drill guide 102. In the case where one or more instruments 100 are used that include a non-movably fixed reference guide (e.g., the reference guides illustrated in FIGS. 1a-b and 4), a particular medical instrument 100 having the desired fixed reference guide can be selected and used during the surgical procedure.

Although the example embodiment illustrated in FIGS. 6-11 includes inserting two anchors, more or fewer anchors are possible. For instance, in an example embodiment, three anchors are inserted into the knee joint structure 204 to secure the knee joint capsule to the knee joint structure 204. In an example, the first and second anchors are about 1 cm to about 2 cm apart, and the second and the third anchors are about 1 cm to about 2 cm apart. In another example, one anchor is used to secure the knee joint capsule to the knee joint structure 204. In yet another example, four or more anchors are used to secure the knee joint capsule to the knee joint structure 204.

Furthermore, in the example of FIGS. 6-11, the anchors are inserted through the medial knee capsule and into the knee joint structure 204. However, in other example embodiments, the anchors are inserted through the lateral capsule and into the knee joint structure 204. Still further, in the example embodiment of FIGS. 6-11, the knee joint structure 204 into which the one or more anchors are inserted is the tibia. However, in other example embodiments, the knee joint structure 204 is the femur.

Although the example embodiment illustrated in FIGS. 6-11 illustrate the joint space 202 as a knee joint, other joint spaces are possible as well. For instance, in other examples, the joint space is a shoulder joint, an elbow joint, or a wrist joint.

In an example embodiment, a method of selecting or defining an anchor placement location(s) is disclosed. The method comprises using at least one of the disclosed medical instruments to select or define the anchor placement location(s). For instance, the method of selecting or defining the anchor placement location(s) can comprise using medical instrument 100, 100c, 100e, and/or 220.

The disclosed methods and systems described herein beneficially provide improved methods and systems for anchor placement in a joint. The disclosed methods and systems allow for easily and accurately inserting the one or more anchors at the desired anchor placement location and the desired anchor placement angle. As a result, the disclosed methods and systems beneficially improve both the efficiency and accuracy of anchor placement during surgical procedures for repairing a joint.

The term "substantially" refers to a recited characteristic need not be achieved exactly, but that deviations or variations, including for example, tolerances, measurement error, measurement accuracy limitations and other factors known to persons having skill in the art, can occur in amounts that do not preclude the effect the characteristic was intended to provide.

The term "about" in association with a numerical value refers to a value that can vary by 5%. For example, a value of "about 100" means 95 to 105 (or any value between 95 and 105).

The term "joint space" refers to the space in a joint between two bones.

The term "joint capsule" refers to an envelope surrounding a synovial joint, where the joint capsule includes an outer fibrous layer or membrane and an inner synovial layer or membrane. On the inside of the joint capsule, articular cartilage covers the end surfaces of the bones that articulate within that joint. The joint capsule surrounds the bones joined by the synovial joint to provide strength and lubrication.

The term "knee joint capsule" refers to an envelope that surrounds the knee joint and includes an outer fibrous layer or membrane and an inner synovial layer or membrane. The knee joint capsule surrounds the bones of the knee to provide strength and lubrication.

The term "knee joint structure" refers to the portions of the knee enveloped by and surrounding the knee joint capsule. In an example embodiment, the knee joint structure includes meniscus, the tibia, the femur, tibial periosteum, and femoral periosteum.

The term "knee joint line" refers to the line through the most distal points of the medial and lateral femoral condyles in the coronal plane, or the line through the most distal point of the femur perpendicular to the anatomical axis of the tibial shaft in the sagittal plane.

The term "tibial plateau" refers to the smooth bony surface of either the lateral condyle or the medial condyle of the tibia that articulates with the corresponding condylar surface of the femur.

The description of the different advantageous arrangements has been presented for purposes of illustration and description, and is not intended to be exhaustive or limited to the embodiments in the form disclosed. Many modifications and variations will be apparent to those of ordinary skill in the art. Furthermore, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A method comprising: inserting a piercing rod through a knee capsule, beneath a meniscus, and above a tibial plateau; advancing a reference guide attached to a drill guide over the piercing rod; such that the piercing rod is within the reference guide, wherein the drill guide defines an anchor placement location that has a predetermined offset from the piercing rod; and advancing a drill pin through the drill guide and drilling a hole into a joint structure at the defined anchor placement location.

2. The method of claim 1, further comprising: advancing an anchor through the drill guide; and placing the anchor in the hole.

3. A method comprising: inserting a piercing rod through a knee capsule, beneath a meniscus, and above a tibial plateau; advancing a reference guide attached to a drill guide over the piercing rod, wherein the drill guide defines an anchor placement location that has a predetermined offset from the piercing rod; and advancing a drill pin through the drill guide and drilling a hole into a joint structure at the defined anchor placement location, wherein an anchor at the anchor placement location can secure a knee joint capsule to the joint structure at a point of capsular disruption, the method further comprising: determining a distance of the point of capsular disruption from a position beneath the meniscus and above the tibial plateau; and adjusting a position of the reference guide relative to the drill guide based the determined distance.

4. The method of claim 3, further comprising: advancing a second reference guide attached to the drill guide over the piercing rod, wherein the drill guide defines a second anchor placement location that has a second predetermined offset from the piercing rod; advancing a drill pin through the drill guide and drilling a second hole into the joint structure at the defined second anchor placement location; advancing a second anchor through the drill guide; and placing the second anchor into the second hole.

5. The method of claim 3, further comprising: advancing a second reference guide attached to a second drill guide over the piercing rod, wherein the second drill guide defines a second anchor placement location that has a second predetermined offset from the piercing rod; advancing a drill pin through the second drill guide and drilling a second hole into the joint structure at the defined second anchor placement location; advancing a second anchor through the second drill guide; and placing the second anchor into the second hole.

6. The method of claim 1, wherein inserting a piercing rod through a knee capsule, beneath a meniscus, and above a tibial plateau comprises inserting a needle or wire through the knee capsule, beneath the meniscus, and above the tibial plateau.

7. The method of claim 1, further comprising: advancing a second reference guide attached to the drill guide over the piercing rod, wherein the drill guide defines a second anchor placement location that has a second predetermined offset from the piercing rod; advancing a drill pin through the drill guide and drilling a second hole into the joint structure at the defined second anchor placement location; advancing a second anchor through the drill guide; and placing the second anchor into the second hole.

8. The method of claim 1, further comprising: advancing a second reference guide attached to a second drill guide over the piercing rod, wherein the second drill guide defines a second anchor placement location that has a second predetermined offset from the piercing rod; advancing a drill pin through the second drill guide and drilling a second hole into the joint structure at the defined second anchor placement location; advancing a second anchor through the second drill guide; and placing the second anchor into the second hole.

9. The method of claim 3, further comprising: advancing an anchor through the drill guide; and placing the anchor in the hole.

10. The method of claim 3, wherein inserting a piercing rod through a knee capsule, beneath a meniscus, and above a tibial plateau comprises inserting a needle or wire through the knee capsule, beneath the meniscus, and above the tibial plateau.

* * * * *